United States Patent
Fontana et al.

Patent Number: 6,083,424
Date of Patent: Jul. 4, 2000

[54] COMPOSITIONS TO REMOVE WATER AND/OR SOLVENTS

[75] Inventors: Simonetta Fontana; Rossella Silvani, both of Milan, Italy

[73] Assignee: Ausimont S.p.A.

[21] Appl. No.: 09/046,550

[22] Filed: Mar. 24, 1998

[30] Foreign Application Priority Data

Mar. 25, 1997 [IT] Italy ................... MI97A0684

[51] Int. Cl.⁷ .............. B01F 1/00; C11D 17/00; C11D 3/37; C11D 9/00; B08B 3/14
[52] U.S. Cl. ............... 252/364; 510/365; 510/475; 510/506; 134/42
[58] Field of Search ................ 252/364; 510/365, 510/475, 506; 134/42

[56] References Cited

U.S. PATENT DOCUMENTS

| | | | |
|---|---|---|---|
| 3,242,218 | 3/1966 | Miller et al. | 260/615 |
| 3,665,041 | 5/1972 | Sianesi et al. | 260/615 A |
| 3,715,378 | 2/1973 | Sianesi et al. | 260/463 |
| 3,810,874 | 5/1974 | Mitsch et al. | 260/75 |
| 3,957,672 | 5/1976 | Zisman et al. | |
| 4,523,039 | 6/1985 | Lagow et al. | 568/615 |
| 4,845,268 | 7/1989 | Ohsaka et al. | 560/184 |
| 5,051,158 | 9/1991 | Marchionni et al. | 204/157.6 |
| 5,084,146 | 1/1992 | Huang | 205/414 |
| 5,144,092 | 9/1992 | Marraccini et al. | 568/615 |
| 5,298,083 | 3/1994 | Van Der Puy et al. | 134/42 |
| 5,654,263 | 8/1997 | Abusleme et al. | 510/365 |
| 5,658,962 | 8/1997 | Moore et al. | 521/114 |
| 5,756,002 | 5/1998 | Chen et al. | 252/364 |
| 5,780,414 | 7/1998 | Silvani et al. | 510/365 |

FOREIGN PATENT DOCUMENTS

| | | |
|---|---|---|
| 0 148 482 | 7/1985 | European Pat. Off. |
| 0 280 312 A2 | 8/1988 | European Pat. Off. |
| 0 695 775A1 | 2/1996 | European Pat. Off. |
| 0 805 199 A2 | 3/1997 | European Pat. Off. |
| 1104482 | 2/1968 | United Kingdom |
| 1194431 | 7/1970 | United Kingdom |
| WO 95/3274 | 11/1995 | WIPO |

*Primary Examiner*—Gabrielle Brouillette
*Assistant Examiner*—LaToya Cross
*Attorney, Agent, or Firm*—Arent Fox Kintner Plotkin Kahn

[57] ABSTRACT

Compositions used to remove traces of water and/or organic solvents and/or oils from the component surfaces, comprising:

i) hydrofluoropolyethers having the general formula:

$$HF_2CO(CF_2O)_n(CF_2CF_2O)_mCF_2H$$

ii) fluorinated additive having a structure selected from the following:

$$T-OR_f(CFY)-L \quad (I)$$

$$L-CF_2OR_fCF_2-L \quad (II)$$

with $L=X-CH_2CH_2(OCH_2CH_2)_{n°}B$
wherein $X=CH_2O$, $CH_2NR"$, $CONR"$, $CH_2OCH_2CH_2NR"$, $CH_2OCOCH_2O$;
$n°=0–50$; $B=NHC(CH_2OH)_3$, $CH_2O(CH_2OH)_3$;
with $R"=H$, alkyl $C_{1-3}$; $Y=CF_3$ or $F$; T is selected from $-CF_3$, $-C_2F_5$, $-C_3F_7$, $ClCF_2CF(CF_3)-$, $CF_3CFClCF_2-$, $ClCF_2CF_2-$, $ClCF_2-$; $R_f$ is a (per)fluoroalkane and/or (per)fluoro-polyether chain.

14 Claims, No Drawings

COMPOSITIONS TO REMOVE WATER AND/OR SOLVENTS

The present invention relates to solvents suitable as cleaning rinsing agents able to remove traces of water, solvents, oils, greases, waxes, etc. from substrates.

In particular as oils, mineral oils, silicone oils and turpentines can be mentioned; as substrates, surfaces of metal components, plastic and glass material can be mentioned; as solvents, the organic ones, among which hydrocarbons, aliphatic esters, etc., can be mentioned.

The problem is particularly felt in the industry where it is necessary to remove traces of water, organic solvents and oils from the components which come into contact with the above mentioned materials during the cleaning or processing cycles. Substances that the composition of the present invention are able to remove are not mixable in the hydrofluoropolyethers forming the composition itself and therefore their removal cannot take place by simple dissolution, but by displacement. It is evident that after such removal process (de-solving, de-watering and/or de-oiling) the treated components must be completely free from stains or residues.

A product meeting such requirements must not degrade, attack or modify the surface of the treated components. Moreover, such product must be non-flammable, non toxic and thermally stable. It must also be environmentally safe and, in particular, have no impact on the ozone layer (zero ODP) and not favour the greenhouse effect (low GWP).

The technical problem that is to be solved by the present invention relates to the need of the availability of non toxic solvents having the above characteristics. This problem is particularly felt since the laws of the various countries have banned or are going to ban the use of most solvents used so far owing to problems of the impact on the ozone layer. As an example of solvents which will no longer be used due to their impact on the ozone layer, chlorinated solvents, chlorofluorocarbons (CFC) and in the future also hydrochlorofluorocarbons (HCFC) can be mentioned. For many years chlorofluorocarbons (CFC), mainly CFC-113, have been used in various washing and drying processes. The above mentioned CFC meet quite completely the properties indicated above except for the high ODP which has even caused the banning.

It has been unexpectedly and surprisingly found by the Applicant a composition able to remove water, organic solvents, turpentines and mineral oils from the surfaces of components having the characteristics mentioned above.

It is therefore an object of the present invention a composition comprising:

i) hydrofluoropolyethers having the general formula:

$$HF_2CO\ (CF_2O)_n(CF_2CF_2O)_mCF_2H$$

wherein n and m are integers comprised between 0 and 20, excluding the case wherein m and n are contemporaneously 0, and having boiling point between 30° and 200° C., preferably between 60° and 150° C., and having a molar ratio O/C comprised between 0.5 and 1;

ii) fluorinated additive having a structure selected among the following:

$$T—OR_f(CFY)—L \quad (I)$$

$$L—CF_2OR_fCF_2—L \quad (II)$$

wherein

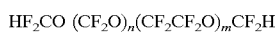
L=X—CH$_2$CH$_2$(OCH$_2$CH$_2$)$_{n°}$B wherein

X=CH$_2$O, CH$_2$NR", CONR", CH$_2$OCH$_2$CH$_2$NR", CH$_2$OCOCH$_2$O;

n°=0–50;

B=NHC(CH$_2$OH)$_3$, OC(CH$_2$OH)$_3$;

with R"=H, alkyl C$_{1-3}$;

Y=CF$_3$ or F;

R$_f$ is (per)fluoroalkane radical from 4 to 20 C atoms or (per)fluoropolyether radical comprising repeating units statistically distributed along the polymer chain selected from:

(CF$_2$CF$_2$O), (CFYO) wherein Y is equal to F or CF$_3$, (C$_3$F$_6$O), (CF$_2$(CF$_2$)$_z$O) wherein z is an integer equal to 2 or 3, (CF$_2$CF(OR$_f$)O), (CF(OR$_f$)O) wherein R$_f$ is equal to —CF$_3$, —C$_2$F$_5$, —C$_3$F$_7$; CR$_4$R$_5$CF$_2$CF$_2$O wherein R$_4$ and R$_5$ are equal to or different from each other and selected from H, Cl or perfluoroalkyle, for instance with 1–4 C atoms;

T is selected from —CF$_3$, —C$_2$F$_5$, —C$_3$F$_7$, ClCF$_2$CF(CF$_3$)—, CF$_3$CFClCF$_2$—, ClCF$_2$CF$_2$—, ClCF$_2$—.

The number average molecular weight of T—OR$_f$ or CF$_2$R$_f$CF$_2$, when R$_f$ is a (per)fluoropolyether, is comprised between 500 and 1,200.

In particular the following R$_f$ (per) fluoropolyethers can be mentioned as preferred:

(a) —(CF$_2$CF(CF$_3$)O)$_a$(CFYO)$_b$—
wherein Y is F or CF$_3$; a and b are integers such that the molecular weight is in the range indicated above; a/b is comprised between 10 and 100;
or the-repeating units indicated in a) can be linked as follows:
—(CF$_2$CF(CF$_3$)O)$_a$(CFYO)$_b$—CF$_2$(R'$_f$)$_x$CF$_2$—O—(CF$_2$CF(CF$_3$)O)$_a$(CFYO)$_b$— wherein R'$_f$ is a (per)fluoroalkylene group, for instance from 1 to 4 C;

(b) —(CF$_2$CF$_2$O)$_c$(CF$_2$O)$_d$(CF$_2$(CF$_2$)$_z$O)$_h$—
wherein c, d and h are integers such that the molecular weight is comprised in the range indicated above; c/d is comprised between 0.1 and 10; h/(c+d) is comprised between 0 and 0.05, z has the value indicated above, h can also be equal to 0;

(c) —(CF$_2$CF(CF$_3$)O)$_e$(CF$_2$CF$_2$O)$_f$(CFYO)$_g$—
wherein Y is F or CF$_3$; e, f, g are integers such that the molecular weight is comprised in the range indicated above; e/(f+g) is comprised between 0.1 and 10, f/g is comprised between 2 and 10;

(d) —(CF$_2$O)$_j$(CF$_2$CF(OR$_{f'}$)O)$_k$(CF(OR$_{f'}$)O)$_l$—
wherein: R$_{f'}$ is —CF$_3$, —C$_2$F$_5$, —C$_3$F$_7$; j,k,l are integers such that the molecular weight is comprised in the range indicated above; k+l and j+k+l are at least equal to 2, k/(j+l) is comprised between 0.01 and 1000, 1/j is comprised between 0.01 and 100;

(e) —(CF$_2$(CF$_2$)$_z$O)$_s$—
wherein s is an integer such as to give the molecular weight indicated above, z has the meaning already defined;

(f) —(CR$_4$R$_5$CF$_2$CF$_2$O)$_j'$, —
wherein R$_4$ and R$_5$ are equal to or different from each other and selected from H, Cl or perfluoroalkyle, for instance from 1 to 4 C atoms, j' being an integer such that the molecualr weight is that indicated above; said unit inside the (per)fluoropolyoxyalkylene chain being linked each other as follows:
wherein R'$_f$ is a (per)fluoroalkylene group, for instance from 1 to 4 C atoms; p' and q' are integers such that the molecular weight is that indicated above;

(g) —(CF(CF$_3$)CF$_2$O)$_{j''}$— j'' being an integer such as to give the molecular weight indicated above; said units being linked each other inside the (per)fluoropolyoxyalkylene chain as follows to have a bivalent radical:

—(CF$_2$CF(CF$_3$)O)$_{a'}$—CF$_2$(R'$_f$)$_x$CF$_2$—O—(CF(CF$_3$)CF$_2$O)$_{b'}$— wherein R'$_f$ has the meaning indicated above, x is 0 or 1, a' and b' are integers and a'+b' is at least 1 and such that the molecualr weight is that indicated above.

These structures comprising the indicated repeating units and the methods for preparing them are described in GB 1,104,482, U.S. Pat. Nos. 3,242,218, 3,665,041, 3,715,378, EP 148.482, U.S. Pat. Nos. 4,523,039, 5,144,092, and for the functional derivatives see U.S. Pat. No. 3,810,874. All these patents are incorporated herein by reference.

When R$_f$ is a (per)fluoroalkane type, preferably it has from 8 to 12 C atoms. R$_f$ of (per)fluoropolyether type is preferred.

For the de-watering applications the n° value present in L of the formulae (I) and (II) is such that the product is not soluble in water. In this case the preferred n° values are comprised between 0 and 3.

For the de-solving and de-oiling applications, n° can preferably range between 1 and 40.

The composition object of the present invention is able to remove, without solubilizing them, water, solvents based on hydrocarbon mixtures, silicone and fluorosilicone oils, hydrogenated base oils. The silicone-based oils are well known and in general are polymethylsiloxanes having a different viscosity, for intance from 50 to 30,000 cSt. Among the fluorosilicones trifluoropropylmethylpolysiloxane can for instance be mentioned. As hydrogenated base oils, products based on mineral oils derived from petroleum or on synthetic or semi-synthetic oils are meant. Mineral turpentines, polyalphaolefins and mineral oils such as for instance the dimer ester can be mentioned.

Among the organic solvents, hydrocarbon based solvents or hydrocarbon and aliphatic ester mixtures, such as for instance the commercial product Axarel® 9100, can be mentioned. Hydrofluoropolyethers mentioned at point i) are generally formed by a mixture of components having a different molecular weight, and have boiling points comprised in the ranges previously described. Such products are chemically inert and have a good compatibility with most fluorinated and non fluorinated materials commonly used in the industry. Moreover they are not toxic, do not damage the ozone layer, are not flammable and do not favour the greenhouse effect.

The hydrofluoropolyethers of the present invention are obtained by decarboxylation processes of the alkaline salts obtained by hydrolysis and salification of the corresponding acylfluorides, by means of processes known in the art. For instance the decarboxylation is carried out in the presence of hydrogen-donor compounds, for instance water, at temperatures in the range 140°–170° C. and under a pressure of at least 4 atm. See for instance EP 695,775 and the examples reported therein; this patent is herein incorporated by reference.

The very great efficacy of the compositions of the present invention allows the use of amounts of additive generally lower than or equal to 0.1% by weight, preferably lower than 0.05%. This represents a further advantage of the present invention since the additives can leave traces on the substrate and/or produce foams when used in high concentrations as it is generally required for the additives of the prior art.

When R$_f$ is of (per)fluoroalkane type the additives are obtained by using similar reactions.

For the additive preparation processes, the Patents indicated above can be used, for instance starting from a monofunctional or bifunctional (per)fluoropolyether, that is, having —COF end groups, according to U.S. Pat. No. 3,810,874, herein incorporated by reference.

For instance, for preparing additives wherein X=CH$_2$O and B=NHC(CH$_2$OH)$_3$ one starts from the product having —COF end groups. The —COF group is reduced with metal hydrides to give the alcohol derivative —CH$_2$OH which by treatment with one mole of ethylene oxide gives the monoaddition product —CH$_2$O—CH$_2$CH$_2$OH. The corresponding tosyl derivative is prepared by reaction with the paratoluensulphonic acid chloride. The tosyl derivative is then reacted with a great excess of tris(hydroxymethyl) aminomethane. For the other linking groups X, U.S. Pat. No. 3,810,874 mentioned above can be used.

The compositions of the invention allow a removal of water and oily subtances even higher than 99%. The amount which remains on the substrate is easily removable by rinsing in hydrofluoropolyethers vapours.

The substrates which can be treated with the composition of the present invention are generally both of organic and inorganic type. Metals, ceramic or glass materials, polymeric substrates can be mentioned.

The removal of water traces, organic solvents and oily traces can be carried out according to known techniques; dipping or spray. In the dipping the contact between the composition of the invention and the surface to be cleaned can be improved by using an ultrasonic bath, which allows to remove more efficaciously also the solid contaminants.

A further advantage of the composition of the present invention resides in that it removes the substances indicated above without solubilizing them, thus allowing the recycling of the composition itself by using simple physical operations without having to use to distillation. Therefore the removal process according to the present invention results very simplified.

The present invention will now be better illustrated by the following application examples, which have a merely illustrative purpose but not limitative of the aim of the invention.

EXPERIMENTAL PART

Example 1

(de-watering)

The samples used (metal flat specimen and electronic components) were immersed in main water. They were then weighed and successively immersed for 1–2 minutes in a bath containing hydrofluoropolyether having the following structure:

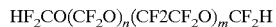

HF$_2$CO(CF$_2$O)$_n$(CF2CF$_2$O)$_m$CF$_2$H having a distillation range comprised between 100° and 120° C., number average molecular weight Mn equal to 380 and O/C ratio equal to 0.56.

The hydrofluoropolyether is additived with 0.1% by weight of the fluorinated additive having the following structure:

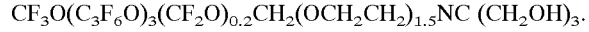

CF$_3$O(C$_3$F$_6$O)$_3$(CF$_2$O)$_{0.2}$CH$_2$(OCH$_2$CH$_2$)$_{1.5}$NC (CH$_2$OH)$_3$.

Then the samples were allowed to dry and later on weighed to determine the removed amount of water remained on the surface which resulted higher than 99.8% by weight.

Example 2 (Comparative)

The test of Example 1 was repeated by using hydrofluoropolyether without the addition of the fluorinated additive. The amount of water removed resulted lower than 70%.

Example 3

(de-solving)

The hydrofluoropolyether of Examples 1–2 was used to verify the capabiity of removing organic solvents from the surface of the considered samples. A known amount of solvent was uniformly distributed on the surface of the above samples, which were successively dipped in a bath containing hydrofluoropolyether additived with 0.1% by weight of the same fluorinated additive of Example 1.

As organic solvent the commercially available solvent Axarel® 9100 was used. Such solvent is formed by a mixture of aliphatic hydrocarbons (96–99% by weight) and of aliphatic esters (4–1% by weight). It has a boiling point in the range 221°–277° C., flash point of 96° C. and results inflammable. The test has been carried out as in Examples 1–2 and the amount of Axarel® 9100 removed resulted higher than 99.5% by weight.

Example 4 (Comparative)

The test described in Example 3 was repeated by utilizing pure hydrofluoropolyether without the addition of the fluorinated additive. The amount of Axarel® 9100 removed from the sample surface resulted lower than 95% by weight.

Example 5

(de-oiling)

The hydrofluoropolyether of Examples 1–4 was used to verify the capability of removing mineral oils and turpentines from the surface of the considered samples. As described in the preceding Examples, a known amount of mineral oil was uniformly distributed on the sample surface. Such samples were successively dipped in a bath containing hydrofluoropolyether additived with 0.1% by weight of the fluorinated additive of Example 1. The mineral oils considered were the following:

Polyalphaolefin (PAO®) having viscosity equal to 40 cSt commercialized by Itec;

Dimer ester PRIOLUBE® 3967 commercialized by Unichem International;

Dearomatized turpentine D® 40 commercialized by Exxon. The removed oil amounts are reported in Table I.

Example 6 (Comparative)

The test of Example 5 was repeated by utilizing only the pure hydrogenfluoropolyether without the addition of the fluorinated additive. The removed oil amounts are reported in Table II.

TABLE I

| USED OIL | AMOUNT OF OIL REMOVED |
|---|---|
| PAO | higher than 99.5% by weight |
| PRIOLUBE ® 3967 | higher than 99% by weight |
| D ® 40 | higher than 99.5% by weight |

TABLE II

| USED OIL | AMOUNT OF OIL REMOVED |
|---|---|
| PAO | lower than 90% by weight |
| PRIOLUBE ® 3967 | lower than 85% by weight |
| D ® 40 | lower than 90% by weight |

We claim:

1. A composition used to remove traces of water and/or organic solvents and/or oils from the surfaces of components, comprising:

i) hydrofluoropolyethers having the formula:

$$HF_2CO(CF_2O)_n(CF_2CF_2O)_mCF_2H$$

wherein n and m are integers comprised between 0 and 20, excluding the case wherein m and n are contemporaneously 0, and having boiling point between 30 and 200° C., and having a molar ratio O/C comprised between 0.5 and 1;

ii) fluorinated additives having a structure selected from the following:

$$T-OR_f(CFY)-L \qquad (I)$$

and $$L-CF_2OR_fCF_2-L \qquad (II)$$

wherein L=X—CH$_2$CH$_2$(OCH$_2$CH$_2$)$_{n^o}$B
wherein X=CH$_2$O, CH$_2$NR", CONR", CH$_2$OCH$_2$CH$_2$NR" or CH$_2$OCOCH$_2$O;
wherein R"=H or a C$_1$–C$_3$ alkyl
n$^o$=0–50;
B=NHC(CH$_2$OH)$_3$ or OC(CH$_2$OH)$_3$;
Y=CF$_3$ or F;
T is selected from —CF$_3$, —C$_2$F$_5$, —C$_3$F$_7$, ClCF$_2$CF(CF$_3$)—, CF$_3$CFClCF$_2$—, ClCF$_2$CF$_2$— and ClCF$_2$—;
R$_f$ is selected from the radicals of (per)fluoroalkane having from 4 to 20 carbon atoms, and (per)fluoropolyether comprising repeating units statistically distributed along the polymer chain selected from:
—CF$_2$CF$_2$O; CFYO, wherein Y is equal to F or CF$_3$; C$_3$F$_6$O; CF$_2$(CF$_2$)$_z$O, wherein z is an integer equal to 2 or 3; CF$_2$CF(OR$_f$)O, wherein R$_f$ is equal to —CF$_3$, —C$_2$F$_5$, —C$_3$F$_7$; and CR$_4$R$_5$CF$_2$CF$_2$O wherein R$_4$ and R$_5$ are equal to or different from each other and selected from H, Cl and perfluoroalkyl.

2. Composition according to claim 1 wherein the component ii) has formula (I).

3. Composition according to claim 1 wherein for de-watering applications the component ii) has n$^o$ value between 0 and 3.

4. Composition according to claim 1 wherein for de-solving and/or de-oiling applications the component ii) has n$^o$ value between 1 and 40.

5. Composition according to claim 1 wherein R$_f$ is a (per)fluoropolyether radical comprising the repeating units (CFYO), wherein Y is equal to F or CF$_3$, and (C$_3$F$_6$O).

6. Composition according to claim 1 wherein the component ii) has number average molecular weight of the T—OR$_f$— or —CF$_2$R$_f$CF$_2$— comprised between 500 and 1,200 when R$_f$ is a (per)fluoropolyether radical.

7. Composition according to claim 1 wherein in the component ii) R$_f$ is selected from (per) fluoropolyethers having the following repeating units:

(a) (CF$_2$CF(CF$_3$)O)$_a$(CFYO)$_b$ wherein Y is F or CF$_3$; a and b are integers such that the molecular weight is comprised between 300 and 1500 and ratio a/b is comprised between 10 and 100; or the repeating units indicated in (a) can be linked as follows: (CF$_2$CF(CF$_3$)O)$_a$(CFYO)$_b$—CF$_2$(R'$_f$)$_x$CF$_2$—O—(CF$_2$CF(CF$_3$)O)$_a$(CFYO)$_b$ wherein R'$_f$ is a fluoroalkylene group;

(b) (CF$_2$CF$_2$O)$_c$(CF$_2$O)$_d$(CF$_2$(CF$_2$)$_z$O)$_h$ wherein c, d and h are integers such that the molecular weight is comprised in the range indicated in (a); the ratio c/d is comprised between 0.1 and 10; the ratio h/(c+d) is comprised between 0 and 0.05, z is an integer equal to 2 or 3, h can also be equal to 0;

(c) (CF$_2$CF(CF$_3$)O)$_e$(CF$_2$CF$_2$O)$_f$(CFYO)$_g$ wherein Y is F or CF$_3$; e, f, g are integers such that the molecular weight is comprised in the range indicated in (a); the ratio e/(f+g) is comprised between 0.1 and 10, the ratio f/g is comprised between 2 and 10;

(d) —(CF$_2$O)$_j$(CF$_2$CF(OR$_{f'}$)O)$_k$(CF(OR$_{f'}$)O)$_l$ wherein: R$_{f'}$ is —CF$_3$, —C$_2$F$_5$, —C$_3$F$_7$; j, k, and l are integers such that the molecular weight is comprised in the range indicated in (a); k+l and j+k+l are at least equal to 2, the ratio k/(j+l) is comprised between 0.01 and 1000, and the ratio l/j is comprised between 0.01 and 100;

(e) (CF$_2$(CF$_2$)$_z$O)$_s$ wherein s is an integer to give the molecular weight indicated in (a), z is an integer of 2 or 3;

(f) —(CR$_4$R$_5$CF$_2$CF$_2$O)$_{j'}$ wherein R$_4$ and R$_5$ are equal to or different from each other and selected from H, Cl or perfluoroalkyl, j' being an integer such that the molecular weight is that indicated in (a); and wherein the repeating units in (f) are linked to each other as follows:

(CR$_4$R5CF$_2$CF$_2$)$_{p'}$R'$_f$—O—(CR$_4$R$_5$CF$_2$CF$_2$O)$_{q'}$ wherein R'$_f$ is a fluoroalkylene group p' and g' are integers such that the molecular weight is that indicated in (a);

(g) —(CF(CF$_3$)CF$_2$O)$_{j''}$— j" being an integer to give the molecular weight indicated in (a); and wherein the repeating units in (g) are linked to have a bivalent radical as follows:

(CF$_2$CF(CF$_3$)O)$_{a'}$—CF$_2$(R'$_f$)$_x$CF$_2$—O—(CF(CF$_3$)CF$_2$O)$_{b'}$ wherein R'$_f$ is a fluoroalkylene group x is 0 or 1, a' and b' are integers and a'+b' is at least 1 and such that the molecular weight is that indicated in (a).

8. The composition according to claim 1 wherein the amount of component ii) is lower than or equal to 0.1% by weight.

9. The composition according to claim 1 wherein the substances to be removed are selected from the group consisting of water, mineral oils, silicone oils, turpentines, and solvents based on hydrocarbon mixtures.

10. A method of removing water and/or oily substances and/or organic solvents from organic and/or inorganic substrates comprising contacting said substrates with a composition comprising:

i) hydrofluoropolyethers having the formula:

HF$_2$CO(CF$_2$O)$_n$(CF$_2$CF$_2$O)$_m$CF$_2$H wherein n and m are integers comprised between 0 and 20, excluding the case wherein m and n are contemporaneously 0, and having boiling point between 30 and 200° C. and having a molar ratio O/C comprised between 0.5 and 1;

ii) fluorinated additives having a structure selected from the following:

T—OR$_f$(CFY)—L    (I)

and

L—CF$_2$OR$_f$CF$_2$—L    (II)

wherein L=X—CH$_2$CH$_2$(OCH$_2$CH$_2$)$_{n°}$B wherein X=CH$_2$O, CH$_2$NR", CONR", CH$_2$OCH$_2$CH$_2$NR" or CH$_2$OCOCH$_2$O;

wherein R"=H or a C$_1$–C$_3$ alkyl n°=0–50;

B=NHC(CH$_2$OH)$_3$ or OC(CH$_2$OH)$_3$;

Y=CF$_3$ or F;

T is selected from —CF$_3$, —C$_2$F$_5$, —C$_3$F$_7$, ClCF$_2$CF(CF$_3$)—, CF$_3$CFClCF$_2$—, ClCF$_2$CF$_2$— and ClCF$_2$—;

R$_f$ is selected from the radicals of (per)fluoroalkane having from 4 to 20 carbon atoms, and (per)fluoropolyether comprising repeating units statistically distributed along the polymer chain selected from:

(CF$_2$CF$_2$O); (CFYO) wherein Y is equal to F or CF$_3$; (C$_3$F$_6$O); (CF$_2$(CF$_2$)$_z$O) wherein z is an integer equal to 2 or 3; (CF$_2$CF(OR$_{f'}$)O); (CF(OR$_{f'}$)O) wherein R$_{f'}$ is equal to —CF$_3$, —C$_2$F$_5$, —C$_3$F$_7$; and CR$_4$R$_5$CF$_2$CF$_2$O wherein R$_4$ and R$_5$ are equal to or different from each other and selected from H, Cl and perfluoroalkyl.

11. Fluorinated additives having a structure selected from the following:

T—OR$_f$(CFY)—L    (I)

and

L—CF$_2$OR$_f$CF$_2$—L    (II)

wherein L=X—CH$_2$CH$_2$(OCH$_2$CH$_2$)$_{n°}$B wherein X=CH$_2$O, CH$_2$NR", CONR", CH$_2$OCH$_2$CH$_2$NR" or CH$_2$OCOCH$_2$O;

wherein R"=H or a C$_1$–C$_3$ alkyl n°=0–50;

B=NHC(CH$_2$OH)$_3$ or OC(CH$_2$OH)$_3$;

Y=CF$_3$ or F;

T is selected from —CF$_3$, —C$_2$F$_5$, —C$_3$F$_7$, ClCF$_2$CF(CF$_3$)—, CF$_3$CFClCF$_2$—, ClCF$_2$CF$_2$— and ClCF$_2$—;

R$_f$ is selected from the radicals of (per)fluoroalkane having from 4 to 20 carbon atoms, and (per)fluoropolyether comprising repeating units statistically distributed along the polymer chain selected from:

($CF_2CF_2O$); (CFYO) wherein Y is equal to F or $CF_3$; ($C_3F_6O$); ($CF_2(CF_2)_zO$) wherein z is an integer equal to 2 or 3; ($CF_2CF(OR_f)O$); ($CF(OR_f)O$) wherein $R_f$ is equal to —$CF_3$, —$C_2F_5$, —$C_3F_7$; and $CR_4R_5CF_2CF_2O$ wherein $R_4$ and $R_5$ are equal to or different from each other and selected from H, Cl and perfluoroalkyl.

12. Additives according to claim 11 wherein the component ii) has formula (I).

13. Additives according to claim 11 wherein for de-watering applications the component ii) has $n^o$ value between 0 and 3.

14. Additives according to claim 11 wherein for de-solving and/or de-oiling applications the component ii) has $n^o$ value between 1 and 40.

* * * * *